United States Patent [19]
Jenkins et al.

[11] Patent Number: 5,426,182
[45] Date of Patent: Jun. 20, 1995

[54] POLYSACCHARIDES CONTAINING COMPLEX HYDROPHOBIC GROUPS

[75] Inventors: Richard D. Jenkins, Hurricane; David R. Bassett, Charleston, both of W. Va.; Gregory D. Shay, Cary, N.C.

[73] Assignee: Union Carbide Chemical & Plastics Technology Corporation, Danbury, Conn.

[21] Appl. No.: 887,642

[22] Filed: May 29, 1992

[51] Int. Cl.$^6$ .................. C08B 11/00; A61K 7/06
[52] U.S. Cl. ........................... 536/54; 252/351; 536/31; 536/43; 536/44; 536/90; 536/93; 536/94; 536/96
[58] Field of Search ............. 536/54, 31, 43, 44, 536/90, 93, 94, 96; 252/351

[56] References Cited

U.S. PATENT DOCUMENTS

| | | | |
|---|---|---|---|
| Re. 33,156 | 1/1990 | Shay et al. | 526/301 |
| 1,451,331 | 4/1923 | Dreyfus | 536/91 |
| 3,035,004 | 5/1962 | Glavis | 260/29.7 |
| 3,190,925 | 6/1965 | Stowe | 260/611 |
| 3,277,157 | 10/1966 | Stewart et al. | 260/486 |
| 3,341,627 | 9/1967 | Wilkinson | 260/898 |
| 3,499,876 | 3/1970 | Field et al. | 260/78.5 |
| 3,652,497 | 3/1972 | Junas et al. | 260/47 |
| 3,657,175 | 4/1972 | Zimmerman | 260/29.6 |
| 3,794,608 | 2/1974 | Evani et al. | 260/29.6 |
| 3,894,980 | 7/1975 | DeTammaso | 260/29.6 |
| 3,896,161 | 7/1975 | Borden et al. | 260/486 |
| 3,915,921 | 10/1975 | Schlatzer, Jr. | 260/17.4 |
| 3,940,351 | 2/1976 | Schlatzer, Jr. | 260/17.4 |
| 3,960,935 | 6/1976 | Semour | 260/485 |
| 4,008,202 | 2/1977 | Evani et al. | 260/47 |
| 4,075,411 | 2/1978 | Dickstein | 560/224 |
| 4,079,028 | 3/1978 | Emmons et al. | 260/29.6 |
| 4,085,167 | 4/1978 | Lewis et al. | 260/885 |
| 4,128,520 | 12/1978 | Barabas et al. | 260/29.7 |
| 4,138,381 | 2/1979 | Chang et al. | 260/29.6 |
| 4,155,892 | 5/1979 | Emmons et al. | 260/29.2 |
| 4,167,502 | 9/1979 | Lewis et al. | 260/29.6 |
| 4,226,754 | 10/1980 | Yun et al. | 260/29.6 |
| 4,228,277 | 10/1980 | Landoll | 536/90 |
| 4,230,844 | 10/1980 | Chang et al. | 526/210 |
| 4,268,641 | 5/1981 | Koenig et al. | 525/367 |
| 4,338,239 | 7/1982 | Dammann | 524/549 |
| 4,384,096 | 5/1983 | Sonnabend | 526/313 |
| 4,395,524 | 7/1983 | Emmons et al. | 526/307.2 |
| 4,421,902 | 12/1983 | Chang et al. | 526/317 |
| 4,423,199 | 12/1983 | Chang et al. | 526/307.6 |
| 4,426,485 | 1/1984 | Hoy et al. | 524/591 |
| 4,429,097 | 1/1984 | Chang et al. | 526/317 |
| 4,463,151 | 7/1984 | Schutz et al. | 526/307.5 |
| 4,464,524 | 8/1984 | Karickhoff | 526/313 |
| 4,485,209 | 11/1984 | Fan et al. | 524/801 |
| 4,496,708 | 1/1985 | Dehm et al. | 528/76 |
| 4,509,949 | 4/1985 | Huang et al. | 586/558 |
| 4,514,552 | 4/1985 | Shay et al. | 526/301 |
| 4,569,965 | 2/1986 | Engel et al. | 524/544 |
| 4,600,761 | 7/1986 | Ruffner et al. | 526/270 |
| 4,616,074 | 10/1986 | Ruffner | 526/318 |
| 4,663,159 | 5/1987 | Brode, II et al. | 536/90 |
| 4,684,704 | 8/1987 | Craig | 526/330 |
| 4,703,080 | 10/1987 | Shay et al. | 524/555 |
| 4,722,962 | 2/1988 | Shay et al. | 524/548 |
| 4,735,981 | 4/1988 | Rich et al. | 524/247 |
| 4,764,554 | 8/1988 | Tonge | 524/558 |
| 4,801,671 | 1/1989 | Shay et al. | 526/214 |
| 4,916,183 | 7/1990 | Barron et al. | 524/555 |
| 4,939,283 | 7/1990 | Yokota et al. | 558/33 |
| 5,006,596 | 4/1991 | Chen et al. | 524/555 |
| 5,015,711 | 5/1991 | Simonet et al. | 526/301 |
| 5,023,309 | 6/1991 | Kruse et al. | 528/49 |

FOREIGN PATENT DOCUMENTS 2745872 10/1979 Germany.

OTHER PUBLICATIONS

Jenkins, R. D. et al., Associative Polymers with Novel Hydrophobe Structures, ACS Meeting, N. Y., New York, Aug. 26, 1991.

Nemoto, H. et al., J. Org. Chem., 1992, 57, 435.

U.S. Patent Application Serial No. 07/304,258 (D-15741), filed Jan. 31, 1989.

*Primary Examiner*—Ronald W. Griffin
*Attorney, Agent, or Firm*—G. L. Coon

[57] ABSTRACT

Polysaccharides, including hydroxyethyl cellulose, having complex hydrophobic group substitution, provide latex compositions, such as paints, with improved rheology and stability. Improved processes for producing such polysaccharides are also provided.

25 Claims, No Drawings

POLYSACCHARIDES CONTAINING COMPLEX HYDROPHOBIC GROUPS

RELATED APPLICATIONS

U.S. patent application Ser. No. 07/887,647, now U.S. Pat. No. 5,292,843; U.S. patent application Ser. No. 07/887,646; U.S. patent application Ser. No. 07/887,648, U.S. patent application Ser. No. 07/887,673; U.S. patent application Ser. No. 07/887,672, U.S. patent application Ser. No. 07/887,641, now U.S. Pat. No. 5,292,828; U.S. patent application Ser. No. 07/887,643; U.S. patent application Ser. No. 07/887,645; U.S. patent application Ser. No. 07/887,644; and U.S. patent application Ser. No. 07/887,671 all of which are incorporated herein by reference.

BRIEF SUMMARY OF THE INVENTION

TECHNICAL FIELD

This invention relates to polysaccharides and their use in latex compositions and processes, and more particularly to polysaccharides having one or more complex hydrophobic groups covalently bonded thereto, and improved processes for their production in which polysaccharides provide latex compositions with improved rheology and stability.

BACKGROUND OF THE INVENTION

Latex compositions typically have additives which modify the rheology or stability of the composition. Polysaccharides, and in particular cellulosics, have been described as additives to latex compositions for various purposes, including as protective colloids, thickeners, stabilizers or other rheology modifiers. For example, U.S. Pat. No. 4,684,704 describes latex compositions containing hydrophobically modified, hydroxyethyl cellulose-as a protective colloid. U.S. Pat. No. 4,243,802 and U.S. Pat. No. 4,352,916 describe the use of hydrophobically modified, hydroxyethyl cellulose as thickeners, emulsifiers and stabilizers for latex compositions.

Polysaccharides having aryl substituents are known. For instance, U.S. Pat. No. 1,451,331, U.S. Pat. No. 1,502,379, U.S. Pat. No. 1,589,607, and U.S. Pat. No. 1,972,135 describe hydroxyethyl cellulose with arylalkyl, e.g. benzyl, substitution. Japanese Patent Application Publication No. 82-28003 describes benzyl substituted, quaternary nitrogen-containing cellulosics in cosmetics. U.S. Pat. No. 4,663,159 describes water-soluble, cationic polysaccharides containing hydrophobes including arylalkyl or alkylaryl substituents, having various utilities.

DISCLOSURE OF THE INVENTION

This invention relates to polysaccharides having one or more complex hydrophobic groups covalently bonded thereto and to latex compositions and processes using such polysaccharides. The polysaccharides can have an amount of bunching or clustering of hydrophobic groups, complex hydrophobic groups and mixtures thereof such as described in copending U.S. patent application Ser. No. 07/887,641, now U.S. Pat. No. 5,292,828, which is incorporated herein by reference. The latex composition contains water, latex polymer and water-soluble polysaccharide having one or more complex hydrophobic groups. A process for improving the rheology of latex compositions is provided using such polysaccharides. Processes for producing these polysaccharides are also provided. One process comprises reacting a polysaccharide ether with an complex hydrophobe-containing compound wherein the ether substitution on the polysaccharide provides an increase in the amount of hydrophobe substitution reacted onto the polysaccharide. Another process comprises reacting a polysaccharide with a complex hydrophobe-containing glycidyl ether compound.

DETAILED DESCRIPTION

Polysaccharides are generally high molecular weight polymers composed of monosaccharide repeating units joined by glycosidic bonds. Complex hydrophobe substitution of polysaccharides are polysaccharides which have one or more complex hydrophobic substituents.

The hydrophobes useful in this invention can include, for example, substituted and unsubstituted alkyl, aryl, alkylaryl, arylalkyl and the like. Typical hydrophobes include nonylphenyl, octylphenyl, dodecylphenyl, t-butylphenyl, phenylhexyl, naphthyldodecyl, dodecylphenyl and the like.

The complex hydrophobes having at least one active hydrogen useful in this invention can be represented by the formula:

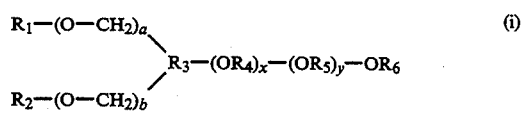

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$.

Other complex hydrophobes having at least one active hydrogen useful in this invention can be represented by the formula:

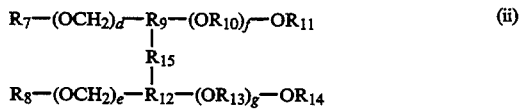

wherein $R_7$ and $R_8$ are the same or different and are hydrogen or a substituted or unsubstituted monovalent hydrocarbon residue, $R_{11}$ and $R_{14}$ are the same or different and are hydrogen, a substituted or unsubstituted monovalent hydrocarbon residue or an ionic substituent, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ and $R_{14}$ or having greater than 2 pendant carbon atoms in the case of $R_9$, $R_{10}$, $R_{12}$, $R_{13}$ and $R_{15}$.

Illustrative substituted and unsubstituted monovalent hydrocarbon residues contain from 1 to about 50 carbon atoms or greater and are selected from alkyl radicals including linear or branched primary, secondary or tertiary alkyl radicals, such as methyl, ethyl, n-propyl, isopropyl, amyl, sec-amyl, t-amyl, 2-ethylhexyl and the like; aryl radicals such as phenyl, naphthyl and the like; arylalkyl radicals such as benzyl, phenylethyl, triphenylmethylethane and the like; alkylaryl radicals such as octylphenyl, nonylphenyl, dodecylphenyl, tolyl, xylyl and the like; and cycloalkyl radicals such as cyclopentyl, cyclohexyl, cyclohexylethyl and the like. The permissible hydrocarbon residues may contain fluorine, silicon, or other non-carbon atoms.

Preferably, the substituted and unsubstituted hydrocarbon residues are selected from alkyl and aryl radicals which contain from about 1 to 30 carbon atoms or greater. More preferably, the alkyl radicals contain from 1 to 18 carbon atoms, while the aryl, arylalkyl, alkylaryl and cycloalkyl radicals preferably contain from 6 to 18 carbon atoms or greater.

In a preferred embodiment of this invention, $R_1$, $R_2$, $R_7$ and $R_8$ can individually be a hydrocarbon radical represented by the formula:

(iii)

wherein $R_{16}$ and $R_{17}$ are as defined for $R_1$, $R_2$, $R_7$ and $R_8$ above, h and i are the same or different and are a value of 0 or 1, and $R_{18}$ is as defined for $R_3$ above. For compounds represented by formulae (i) and (ii), it is understood that each formula (iii) radical in a given compound may be the same or different and the $R_{16}$ and/or $R_{17}$ groups may themselves be a formula (iii) radical to provide complex hydrophobes of a dendritic or of a cascading nature as described below. Further, $R_4$, $R_5$, $R_{10}$ and $R_{13}$ can individually be a hydrocarbon radical represented by the formula:

—CH[(OR$_{19}$)$_j$OR$_{20}$]—    (iv)

wherein $R_{19}$ is as defined for $R_4$, $R_5$, $R_{10}$ and $R_{13}$ above, $R_{20}$ is as defined for $R_6$, $R_{11}$ and $R_{14}$ above, and j is a value of 0 or greater.

Illustrative ionic substituents for $R_6$, $R_{11}$, $R_{14}$ and $R_{20}$ include cationic and anionic substituents such as sulfates, sulfonates, phosphates and the like. $R_6$, $R_{11}$, $R_{14}$ and $R_{20}$ may preferably be an organic residue containing 1 or more hydroxyls or nitrogen derivatives or epoxides or other reactive groups which may or may not contain unsaturation.

Other illustrative terminal groups which are described by $R_6$, $R_{11}$, $R_{14}$ and $R_{20}$ include, for example, hydrocarbon residues which may contain allylic or vinylic unsaturation, acrylic or methacrylic functionality, styryl or alpha-methylstyryl functionality, and the like. Other examples of terminal groups may include hydrocarbon residues of alkyl, aryl, aralkyl, alkaryl, and cycloalkyl radicals which may or may not be substituted with one or more of the following: hydroxyl, carboxyl, isocyanato, amino, mono- or disubstituted amino, quaternary ammonium, sulfate, sulfonate, phosphate, epoxy, and the like and may or may not contain other non-carbon atoms including silicon or fluorine. Also included can be divalent siloxy radicals. Other nonhydrocarbon terminal groups may include sulfates, phosphates, and the like.

Illustrative divalent hydrocarbon residues represented by $R_3$, $R_4$, $R_5$, $R_9$, $R_{10}$, $R_{12}$, $R_{13}$, $R_{15}$, $R_{18}$ and $R_{19}$ in the above formulae include substituted and unsubstituted radicals selected from alkylene, -alkylene-oxy-alkylene-, -arylene-oxy-arylene-, arylene, alicyclic radicals, phenylene, naphthylene, -phenylene-(CH$_2$)$_m$(Q)$_n$(CH$_2$)$_m$-phenylene- and -naphthylene-(CH$_2$)$_m$(Q)$_n$(CH$_2$)$_m$-naphthylene- radicals, wherein Q individually represents a substituted or unsubstituted divalent bridging group selected from —CR$_{21}$R$_{22}$—, —O—, —S—, —NR$_{23}$—, —SiR$_{24}$R$_{25}$— and —CO—, wherein $R_{21}$ and $R_{22}$ individually represent a radical selected from hydrogen, alkyl of 1 to 12 carbon atoms, phenyl, tolyl and anisyl; $R_{23}$, $R_{24}$ and $R_{25}$ individually represent a radical selected from hydrogen and methyl, and each m and n individually have a value of 0 or 1. More specific illustrative divalent radicals represented by $R_3$, $R_4$, $R_5$, $R_9$, $R_{10}$, $R_{12}$, $R_{13}$, $R_{15}$, $R_{18}$ and $R_{19}$ include, e.g., 1,1-methylene, 1,2-ethylene, 1,3-propylene, 1,6-hexylene, 1,8-octylene, 1,12-dodecylene, 1,4-phenylene, 1,8-napthylene, 1,1'-biphenyl-2,2'-diyl, 1,1'-binaphthyl-2,2'-diyl, 2,2'-binaphthyl-1,1'-diyl and the like. The alkylene radicals may contain from 2 to 12 carbon atoms or greater, while the arylene radicals may contain from 6 to 18 carbon atoms or greater. Preferably, $R_3$, $R_4$, $R_5$, $R_9$, $R_{10}$, $R_{12}$, $R_{13}$, $R_{15}$, $R_{18}$ and $R_{19}$ are an alkylene or arylene radical. The permissible divalent hydrocarbon residues may contain fluorine, silicon, or other non-carbon atoms.

Illustrative trivalent hydrocarbon residues represented by $R_3$, $R_9$, $R_{12}$ and $R_{18}$ in the above formulae include substituted and unsubstituted radicals selected from >CH—, >C(R$_{26}$)—, >CR$_{27}$— and the like, wherein $R_{26}$ is a substituted or unsubstituted monovalent hydrocarbon residue as described herein and $R_{27}$ is a substituted or unsubstituted divalent hydrocarbon residue as described herein.

Of course, it is to be further understood that the hydrocarbon residues in the above formulae may also be substituted with any permissible substituent. Illustrative substituents include radicals containing from 1 to 18 carbon atoms such as alkyl, aryl, aralkyl, alkaryl and cycloalkyl radicals; alkoxy radicals; silyl radicals such as —Si(R$_{28}$)$_3$ and —Si(OR$_{28}$)$_3$, amino radicals such as —N(R$_{28}$)2; acyl radicals such as —C(O)R$_{28}$; acyloxy radicals such as —OC(O)R$_{28}$; carbonyloxy radicals such as —COOR$_{28}$; amido radicals such as —C(O)N(R$_{28}$)$_2$ and —N(R$_{28}$)COR$_{28}$; sulfonyl radicals such as —SO$_2$R$_{28}$; sulfinyl radicals such as —SO(R$_{28}$)$_2$; thionyl radicals such as —SR$_{28}$; phosphonyl radicals such as —P(O)(R$_{28}$)$_2$; as well as halogen, nitro, cyano, trifluoromethyl and hydroxy radicals and the like, wherein each $R_{28}$ can be a monovalent hydrocarbon radical such as alkyl, aryl, alkaryl, aralkyl and cycloalkyl radicals, with the provisos that in amino substituents such as —N(R$_{28}$)$_2$, each $R_{28}$ taken together can also compromise a divalent bridging group that forms a heterocyclic radical with the nitrogen atom, in amido substituents such as —C(O)N($R_{28}$)$_2$ and —N($R_{28}$)CO$R_{28}$, each $R_{28}$ bonded to N can also be hydrogen, and in phosphonyl substituents such as —P(O)($R_{28}$)$_2$, one $R_{28}$ can by hydrogen. It is to be understood that each $R_{28}$ group in a particular substituent may be the same or different. Such hydrocarbon substituent radicals could possibly in turn be substituted with a permissible substituent such as already herein outlined above.

Preferred alkylene oxides which can provide random or block oxyalkylene units in the complex hydrophobe compounds represented by formulae (i) and (ii) above include alkylene oxides such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, 1,2-decylene oxide, and higher alpha-olefin epoxides; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorohydrin and epibromohydrin. The preferred alkylene oxides are ethylene oxide and propylene oxide. Also included can be hydrocarbon residues from substituted and unsubstituted cyclic esters or ethers such as oxetane and tetrahydrofuran. It is understood that the compounds represented by formulae (i) and (ii) herein can contain random and/or block oxyalkylene units as well as mixtures of oxyalkylene units. It is further understood that each $R_4$, $R_5$, $R_{10}$, $R_{13}$ and $R_{19}$ group in a particular substituent for all positive values of x, y, f, g and j respectively can be the same or different.

The values of x, y, f, g and j are not narrowly critical and can vary over a wide range. For example, the values of x, y, f, g and j can range from 0 to about 200 or greater, preferably from about 0 to about 100 or greater, and more preferably from about 0 to about 50 or greater. Any desired amount of alkylene oxide can be employed, for example, from 0 to about 90 weight percent or greater based on the weight of the complex hydrophobe compound.

Referring to the general formulae (i) and (ii) above, it is appreciated that when $R_1$, $R_2$, $R_7$ and/or $R_8$ are a hydrocarbon residue of formula (iii) above, the resulting compound may include any permissible number and combination of hydrophobic groups of the dendritic or cascading type. Such compounds included in the above general formulae should be easily ascertainable by one skilled in the art. Illustrative complex hydrophobe compounds having at least one active hydrogen useful in this invention and processes for preparation thereof are disclosed in copending U.S. patent application Ser. No. 07/887,648, which is incorporated herein by reference.

In a preferred embodiment of this invention, the structure shown in formula (iii) can be a residue of the reaction product between epichlorohydrin and an alcohol, including those alcohols whose residues can be described by formula (iii), or a phenolic, or a mixture thereof. The structures which result can be described as complex hydrophobes of a dendritic or of a cascading nature. Pictorially, they can be described as shown below:

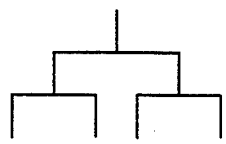

The degree of hydrophobe and complex hydrophobe substitution, i.e. DS, defined as the average moles of hydrophobe and complex hydrophobe substituents per mole of polysaccharide repeat unit, may vary depending upon the presence of other substituents, type of hydrophobe and complex hydrophobe and type of polysaccharide. Generally, the DS of the hydrophobe is greater than zero, preferably from 0.001 to about 0.1 or greater, and most preferably from 0.005 to about 0.03.

The polysaccharides with complex hydrophobic groups and optionally hydrophobic groups include polymers of repeating units represented by the structural formula:

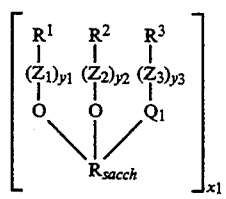

I

In Formula I, for each repeating unit individually:
$Q_1$ is

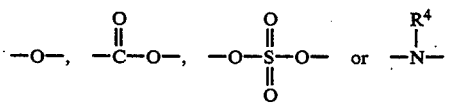

wherein $R^4$ is

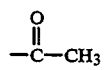

or a mixture of hydrogen and

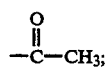

$R_{sacch}$ is the residue of a polysaccharide repeat unit and may include additional reactive groups, as in xanthan gum;

$x_1$ is from about 50 to about 20,000;

each $Y_1$, $Y_2$ and $Y_3$ is 0 or 1;

each $Z_1$, $Z_2$ and $Z_3$ is a divalent connecting segment; and each $R^1$, $R^2$ and $R^3$ is individually hydrogen, a substituted or unsubstituted hydrocarbon residue or a nitrogen-, oxygen-, sulfur- or carboxyl-containing hydrocarbon residue or $R_h$, wherein $R_h$ is the residue of a substituted or unsubstituted complex hydrophobe compound; provided that when $R^1$ $R^2$ or $R^3$ is hydrogen then $Y_1$, $Y_2$ or $Y_3$ respectively is 0, and one or more repeating units have one or more $R^1$, $R^2$ or $R^3$ which is $R_h$.

In Formula I, $Q_1$ is preferably oxygen providing anhydroglucose repeat units, and most preferably cellulose. The number of repeat units, defined by $x_1$, is preferably from about 50 to about 20,000 and most preferably from about 250 to about 4,000, providing a molecular weight of from several thousand up to several million. The molecular weight of the polysaccharide may be varied using well established procedures, such as controlled degradation.

In Formula I, the ether substituents, i.e. $(Z_1)_{Y_1}$—$R^1$, $(Z_2)_{y2}$—$R^2$ and $(Z_3)_{y3}$—$R^3$, are usually hydrogen with some hydrophobic groups, complex hydrophobic groups or mixtures thereof present. Since only one or more repeating units must have one or more $R_h$, not every polysaccharide repeat unit must have an hydrophobic group or complex hydrophobic group. Typical ether substituents include, but are not limited to, one or more of the following: hydrogen, i.e. —H; unsubstituted hydrocarbyl such as —$CH_3$, —$CH_2CH_3$, —$CH_2C_6H_5$, or —$C_{16}H_{33}$; nitrogen-, oxygen-, sulfur- or carboxyl-containing hydrocarbyl such as —$CH_2CH_2OH$; —$CH_2COOH$; —$CH_2COO^-Na^+$ or

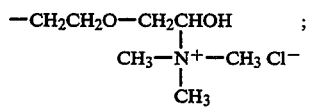

alkylaryl hydrophobic groups with or without connecting segments, including the alkylaryl hydrophobic groups described previously, such as

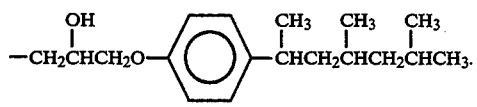

Preferably the ether substituents also include hydroxyethyl, i.e. —$CH_2CH_2OH$, in an amount sufficient to provide water solubility.

In Formula I, the divalent connecting segment, represented by $Z_1$, $Z_2$ and $Z_3$, designates the portion of the ether substituent which is provided between the cellulose ether oxygen, or Q group, and the main portion of the substituent, such as a complex hydrophobic group. When $R^1$ $R^2$ or $R^3$ is hydrogen, i.e. when the group represented is an unsubstituted hydroxyl, there is no connecting segment and $Y_1$, $Y_2$ or $Y_3$ is correspondingly 0. When $R^1$, $R^2$ or $R^3$ is not hydrogen, then a connecting segment may or may not be provided. Generally, the connecting segment represents the residual portion of the compound used to provide a hydrophobic or complex hydrophobic substituent on the polysaccharide. Typical connecting segments, when present, include, but are not limited to: unsubstituted or hydroxy-substituted alkyl or alkoxy groups such as methylene, i.e. —$CH_2$—, ethoxy, i.e. —$CH_2CH_2O$—, or glycidyl ethers, i.e.

Preferably, the connecting segment is absent or present as —$CH_2$- or most preferably as

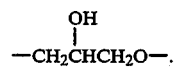

The polysaccharide may contain additional substitution, i.e. other than the hydrophobes and complex hydrophobes, such as may be required to provide the requisite water solubility or other properties. The other substituents may be ionic or nonionic providing nonionic, cationic, anionic or amphoteric polysaccharide. Typical additional substituents include, but are not limited to, one or more of the ether substituents described previously. The amount of additional substitution, i.e. molar substitution defined as the average moles of such substituent per mole of polysaccharide repeat unit, designated MS, is not critical but may be any amount desired. Preferably, the polysaccharide will have a hydroxyethyl MS sufficient to provide water solubility, if needed, and/or improved enzyme resistance if desired. Hydroxyethyl MS may generally be from about 1.5 to about 6, and preferably from about 3 to about 5.

The complex hydrophobe-substituted polysaccharides can be produced from readily available polysaccharide starting materials. These materials include naturally occurring, biosynthesized and derivatized carbohydrate polymers or mixtures thereof. The type of polysaccharide is not critical and includes the entire starch and cellulose families; pectin; chitosan; chitin; the seaweed products such as agar and carrageenan; alginate; the natural gums such as guar, arabic, and tragacanth; bio-derived gums such as dextran and xanthan; and other known polysaccharides. Preferred polysaccharides are cellulosics, including cellulose ethers, which may be derived from conventional materials, such as chemical cotton, cotton linters, wood pulp, alkali cellulose, as well as ether derivatives of these materials.

Cellulose ethers which may be used include, but are not limited to, one or more of the following: hydroxyethyl cellulose; hydroxypropyl cellulose; methyl cellulose; carboxymethyl cellulose; carboxyethyl cellulose; hydroxypropyl ethyl cellulose; hydroxyethyl carboxymethyl cellulose; and the like. A particularly preferred polysaccharide is hydroxyethyl cellulose.

Any reaction condition sufficient to modify the polysaccharide with the hydrophobes may be used, including well established etherification procedures, such as described in U.S. Pat. No. 4,663,159 or U.S. Pat. No. 4,228,277. This reaction may be conducted using any compound having the hydrophobe and a functional group which reacts with the polysaccharide. Typical functional groups include, but are not limited to, one or more of the following: halides, such as chlorides or bromides; oxiranes, such as epoxides including glycidol and its esters; acids, including esters, acid halides or salts thereof, such as carboxylic acids or sulfates; (thio)isocyanates; and halohydrins. Alkylaryl halides may be used but may not be desirable due to problems with corrosivity and having to remove halides from the product. Preferably a glycidyl ether, such as nonyl- or dodecylphenyl glycidyl ether, is used. Other suitable synthetic pathways for preparing water-soluble hydrophobically modified cellulose derivatives are described in Water-Soluble Polymers, Synthesis, Solution Properties and Applications, ACS Symposium Series 467, American Chemical Society (1991), pp. 21-22, incorporated herein by reference.

The hydrophobe and/or complex hydrophobe and/or complex hydrophobe substitution reaction may be conducted at any desired temperature, typically between 20° C. to 125° C. and preferably from about 55° C. to about 95° C., for a time sufficient to provide the desired amount of substituents, typically from about 0.5 hour to about 12 hours or more and preferably from about 1 to 6 hours. The reaction may be conducted with diluent, solvent or catalyst as desired and is typically done in an inert medium in the presence of a caustic catalyst, such as an alkali metal hydroxide or the like material.

In a preferred embodiment, the hydrophobe and/or complex hydrophobe substitution is conducted by reacting a compound having a hydrophobic or complex hydrophobic group with a polysaccharide ether containing another substituent, such as hydroxyethyl, in an amount which increases the efficiency of hydrophobe and/or complex hydrophobe substitution. The MS of other ether substitution, i.e. $MS_E$, may vary depending upon the types of polysaccharide, hydrophobe, complex hydrophobe and other ether substituents present and is generally at least that amount which provides increased hydrophobe substitution as compared to an $MS_E$ of 0. In embodiments when the polysaccharide is cellulose and the other ether substituent is hydroxyethyl, $MS_E$ may range from greater than 0, preferably from about 1.5 to about 6 and most preferably from about 3.5 to about 5 average moles of other ether substituent per mole of polysaccharide repeat unit.

In another preferred embodiment, the hydrophobe and/or complex hydrophobe substitution is conducted using a hydrophobe or complex hydrophobe compound having a functional group which is a glycidyl ether. Such compounds may be represented by the structural formula:

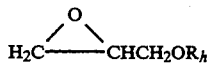

$$\underset{H_2C\text{———}CHCH_2OR_h}{\overset{O}{\diagup \diagdown}} \quad \text{II}$$

wherein $R_h$ is as defined previously in Formula I.

In a typical procedure the hydrophobe and/or complex hydrophobe substitution reaction is carried out in a slurry of the desired polysaccharide in an appropriate aqueous diluent system. Suitable diluents include, but are not limited to, isopropyl alcohol, t-butyl alcohol, sec-butyl alcohol, propyl alcohol, ethanol, methanol, methylethylketone, water, tetrahydrofuran, dioxane, 2-butoxyethanol, 2-ethoxyethanol, acetone, and mixtures of these materials. Suitable weight ratios of diluent to polysaccharide are in the range of about 4:1 to 25:1. Because the reaction is generally carried out heterogeneously, it is important that the diluent system normally not be a solvent for either the starting polysaccharide or the hydrophobe/complex hydrophobe-modified product.

The polysaccharide may be causticized with a suitable caustic catalyst such as sodium hydroxide, potassium hydroxide or lithium hydroxide, with sodium hydroxide being preferred. The molar ratio of caustic to polysaccharide may suitably vary between 0.4 to 2.0. Many polysaccharides that are in contact with any base may be readily degraded by oxygen. It is accordingly necessary to exclude oxygen from the reaction vessel during the time in which caustic is present. It is suitable to carry out the reaction under an inert gas such as nitrogen.

After being causticized with a suitable amount of caustic catalyst, the hydrophobic and/or complex hydrophobic reactant may be added, and the reaction is conducted at a suitable temperature for a time sufficient to provide the desired amount of substitution. Alternately, the polysaccharide may be first reacted with one or more appropriate electrophiles to render the polysaccharide water soluble followed by a sequential reaction with the hydrophobic and/or complex hydrophobic reactant, or the polysaccharide may be simultaneously reacted with one or more electrophiles and the hydrophobic and/or complex hydrophobic reactant. Suitable electrophiles include ethylene oxide, propylene oxide, chloroacetic acid and its salts, 1,3-propane sultone, methyl chloride, ethyl chloride, glycidol, 3-chloro-1,2-propanediol, and 2-chloroethanol.

Latex compositions can be provided having as essential components: water; latex polymer; and the polysaccharide. The kind and amount of latex polymer is not critical, and may be provided based on well established procedures. Typical latex polymers include, but are not limited to, various types such as the following: acrylics; alkyds; celluloses; coumarone-indenes; epoxys; esters; hydrocarbons; maleics; melamines; natural resins; oleo resins; phenolics; polyamides; polyesters; rosins; silicones; styrenes; terpenes; ureas; urethanes; vinyls; and the like. Illustrative latex polymers include, but are not limited to, one or more homo- or copolymers containing one or more of the following monomers: (meth)acrylates; vinyl acetate; styrene; ethylene; vinyl chloride; butadiene; vinylidene chloride; vinyl versatate; vinyl propionate; t-butyl acrylate; acrylonitrile; neoprene; maleates; fumarates; and the like, including plasticized or other derivatives thereof.

The amount of polysaccharide which may be used in the latex composition is not narrowly critical. In the broadest sense, the amount of polysaccharide is that which is an effective amount in providing improved rheology or stability to the latex composition. Typically, the amount of polysaccharide is at least about 0.05, preferably from about 0.15 to about 3, and most preferably from about 0.25 to about 1.5 weight percent of the latex composition.

The amount of latex polymer used in the latex composition is not critical, but may be any amount following well established procedures using latex polymers. Typically, the amount of dry latex polymer is at least about 1, preferably from about 2 to about 50, and most preferably from about 3 to about 40 weight percent of the total latex composition.

The latex composition may optionally contain other components such as those generally used in latex compositions. Typical components include, but are not limited to, one or more of the following: solvents such as aliphatic or aromatic hydrocarbons, alcohols, esters, ketones, glycols, glycol ethers, nitroparaffins or the like; pigments; fillers, dryers; flatting agents; plasticizers; stabilizers; dispersants; surfactants; viscosifiers including polymeric associative thickeners, polysaccharide-based thickeners and so on; suspension agents; flow control agents; defoamers; anti-skinning agents; preservatives; extenders; filming aids; crosslinkers; surface improvers; corrosion inhibitors; and other ingredients useful in latex compositions.

An enhancement of thickening (herein termed "co-thickening") can result upon the addition of a surfactant to an aqueous system containing the polysaccharide polymer of this invention. In some cases the thickening can be enhanced up to about 40 times the viscosity afforded by the polymer alone. A wide range of surfactants may be used in an amount of about 0.1 to 0.5 parts surfactant per part polymer, same basis.

On the basis of an aqueous system containing about 0.1 to 5% by weight of polymer solids, a useful amount of surfactant for optimum co-thickening is about 0.1 to 1.0% by weight of the total system. As indicated, the amounts of polymer and surfactant cothickener may very widely, even outside these ranges, depending on polymer and surfactant type and other components of the aqueous system to be thickened. However, the co-thickening can reach a maximum as surfactant is added and then decreased. Hence, it may be uneconomical to employ surfactant in amounts outside the stated concentrations and polymer/surfactant ratios, but this can be determined in a routine manner in each case.

The surfactants which may be used include nonionics and anionics, singly or in combination, the selection necessarily depending upon compatibility with other ingredients of the thickened or thickenable dispersions of this invention. Cationic and amphoteric surfactants may also be used provided they are compatible with the polymer and other ingredients of the aqueous system, or are used in such small amounts as not to cause incompatibility.

Suitable anionic surfactants that may be used include the higher fatty alcohol sulfates such as the sodium or potassium salt of the sulfates of alcohols having from 8 to 18 carbon atoms, alkali metal salts or amine salts of high fatty acid having 8 to 18 carbon atoms, and sulfonated alkyl aryl compounds such as sodium dodecyl benzene sulfonate. Examples of nonionic surfactants include alkylphenoxypolyethoxyethanols having alkyl groups of about 7 to 18 carbon atoms and about 9 to 40 or more oxyethylene units such as octylphenoxypolyethoxyethanols, dodecylphenoxypolyethoxyethanols; ethylene oxide derivatives of long-chain carboxylic acids, such as lauric, myristic, palmitic, oleic; ethylene oxide condensates of long-chain alcohols such as lauryl or cetyl alcohol, and the like.

Examples of cationic surfactants include lauryl pyridinium chloride, octylbenzyltrimethylammonium chloride, dodecyltrimethylammonium chloride condensates of primary fatty amines and ethylene oxide, and the like.

The foregoing and numerous other useful nonionic, anionic, cationic, and amphoteric surfactants are described in the literature, such as McCutcheon's Detergents & Emulsifiers 1981 Annual, North America Edition, MC Publishing Company, Glen Rock, N.J. 07452, U.S.A., incorporated herein by reference.

In general, solvents and non-solvents (or mixtures of solvents, non-solvents, other organics and volatiles) can be used to manipulate the viscosity of polymer containing systems. For example, mineral spirits can act like a co-thickener. The co-thickening with mineral spirits has utility in textile printing pastes, and in waterborne automotive basecoats. These systems usually contain mineral spirits (because of the pigments used therein), so that the mineral spirits provide an economical way of increasing viscosity and improving the efficiency of the thickener.

Processes for producing latex compositions having improved rheology and stability can be provided by combining the latex polymer and polysaccharide with water following established procedures.

Although not bound by any particular theory it is believed that the polysaccharides control the rheology of the latex composition by two mechanisms. As with other cellulosics, the aqueous phase of the composition is thickened by the presence of a large hydrodynamic volume resulting from the relatively high molecular weight and water of hydration surrounding the polysaccharide. The complex hydrophobic substitution also thickens the latex composition by an associative mechanism wherein the hydrophobes and/or complex hydrophobes interact with each other and hydrophobic portions of the latex polymer or other ingredients present resulting in improved properties such as high viscosity at low shear, improved spatter resistance and improved flow and leveling, while avoiding problems with syneresis, color acceptance, color development and viscosity stability.

Latex compositions and processes using the polysaccharides are provided whereby the polysaccharide may be used as a protective colloid, thickener, stabilizer or other rheology modifier, such as for emulsion polymerization.

The polysaccharide may also be used in a variety of applications other than in latex compositions and processes. Additional applications include, but are not limited to: cosmetics, such as shampoos; biomedicine such as in oral care including toothpaste or in pharmaceuticals including timed- or controlled-release formulations; detergents such as in laundry or surface cleaners; various other timed-release applications including pesticides; and other areas in which a protective colloid, stabilizer, thickener or rheology modifier is desired.

As used herein, the term "complex hydrophobe" is contemplated to include all permissible hydrocarbon compounds having 2 or more hydrophobe groups, e.g., bis-dodecylphenyl, bis-nonylphenyl, bis-octylphenyl and the like.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

This invention can be illustrated by certain of the following examples.

EXAMPLE 1

Preparation of 1,3-Bis(nonylphenoxy)-2-propanol

To a five neck, two liter round bottom flask equipped with an addition funnel, thermometer, nitrogen dispersant tube, mechanical stirred, and a decanting head with a water-cooled condenser were added 220 grams (1.00 mole) of nonylphenol and 250 milliliters of cyclohexane. The solution was then heated to reflux and 2.8 grams (1.3 wt. % based on nonylphenol) of potassium hydroxide in 10 milliliters of water was slowly added to the flask. After essentially all the water was recovered in the decanting head (10 milliliters+1 milliliter formed), 250.7 grams (0.91 mole) of nonylphenyl glycidyl ether as added dropwise. During the addition of the glycidyl ether, the reaction temperature was maintained between 60 and 80° C. After the addition was complete, the solution was refluxed for four hours. The contents of the flask were then washed with a five percent aqueous solution of phosphoric acid, and the organic layer was separated from the water layer and washed twice with deionized water. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180° C. during the distillation to prevent discoloration of the product. The concentrated solution was then refiltered to give 425 grams of a pale-yellow liquid. End-group MW analysis gave a molecular weight of 506.8 (theoretical MW=496.8). Ir and nmr spectra were identical to previously recorded spectra for the compound.

EXAMPLE 2

Preparation of 1,3-Bis(nonylphenoxy)-2-propanol

To a five neck, two liter round bottom flask, equipped with an addition funnel, thermometer, nitrogen dispersant tube, mechanical stirrer, and a decanting head with a water-cooled condenser, were added 300 milliliters of cyclohexane and 451.7 grams (2.05 mole) of nonylphenol. The solution was then heated to reflux and 58.9 grams (1.05 mole) of potassium hydroxide in 60 milliliters of water was slowly added via the addition funnel. After essentially all the water was recovered in the decanting head (60 milliliter+19 milliliters formed), the reaction was cooled to 40° C., and 92.5 grams (1.00 mole) of epichlorohydrin was slowly added. During the addition, the reaction temperature was maintained below 60° C. by controlling the rate of epichlorohydrin addition. After all the epichlorohydrin was added, the solution was allowed to stir for one hour, and then brought to reflux for an additional three hours. The reaction mixture was then filtered under vacuum through a steam-jacketed Buchner funnel to remove the potassium chloride formed as a by-product. The filtration process was performed a total of three times to remove the majority of the salts. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180° C. during the distillation to prevent discoloration of the product. The concentrated solution was then refiltered to give 275 grams of a pale-yellow liquid. End-group MW analysis gave a molecular weight of 459.7 (theoretical MW=496.8). Ir and nmr spectra were identical to previously recorded spectra for the compound.

EXAMPLE 3

Preparation of 5 Mole Ethoxylate of 1,3-Bis(nonylphenoxy)-2-propanol

To a 500 milliliter, stainless steel, high pressure autoclave was charged 200 grams (0.40 mole) of 1,3-bis(nonylphenoxy)-2-propanol, which contained a catalytic amount of the potassium salt of the alcohol as described in Example 1. After purging the reactor with nitrogen, the alcohol was heated to 130° C. with stirring, and 86.9 grams (2.0 mole) of ethylene oxide was added over a two hour period. The reaction temperature and pressure were maintained from 130° C. to 140° C. and 60 psig during the course of the reaction. After the addition of ethylene oxide was complete, the reaction mixture was held at 140° C. for an additional hour to allow all the ethylene oxide to cook out. The reaction mixture was dumped while hot, under nitrogen, and neutralized with acetic acid to yield 285 grams of a pale-yellow liquid.

EXAMPLE 4

Preparation of Adduct of Nonlphenyl Glycidyl Ether and 5 Mole Ethoxylate of 1,3-Bis(nonylphenoxy)-2-propanol To a five neck, one liter, round bottom flask equipped as in Example 1 was added 119.8 grams (0.17 mole) of the 5 mole ethoxylate of 1,3-bis(nonylphenoxy)-2-propanol and 100 milliliters of cyclohexane. The mixture was refluxed (100° C.) for one hour to remove residual water, and then cooled to 50° C. under nitrogen to add 0.5 grams of $BF_3/Et_2O$. Nonylphenyl glycidyl ether (46.0 grams, 0.17 mole) was then added to the flask over a one hour period, and the reaction was heated to reflux. After three hours at reflux, the reaction mixture was transferred to a separatory funnel, while hot, and washed with a saturated aqueous solution of sodium bicarbonate. The organic layer was separated from the water layer, and washed twice with hot deionized water. The washes were performed at 50° C. to facilitate the separation of the two layers. The water and cyclohexane were then evaporated from the organic layer, under vacuum, to yield 145 grams of a pale-yellow, viscous liquid.- End-group molecular weight analysis gave a molecular weight of 880 (theoretical molecular weight=993).

EXAMPLE 5

Preparation of Poly(nonylphenol glycidyl ether)

To a 500 milliliter round bottom equipped with an overhead stirrer, nitrogen inlet, reflux condenser, additional funnel, and temperature controller was charged 1.9 grams of ethanol (22 mmoles) and 200 grams of cyclohexane. The solution was brought to 50° C. Once heated, 0.5 milliliters (4 mmoles) of $BF_3/Et_2O$ was added using a 2 milliliter syringe. Once the acid was added, 100.0 grams of nonylphenol glycidyl ether (362 mmoles) was added dropwise so as to maintain a reaction temperature of 45° C.–55° C. Once the glycidyl ether was added, the solution is refluxed for 3 hours, then cooled to about 50° C.

While hot (<60° C.) the organic was transferred to a separatory funnel and was washed once with 100 milliliters of 5% sodium bicarbonate solution. The aqueous layer was drained and the organic was washed two more times with 100 milliliter portions of deionized water. The aqueous layers were decanted and the organic was dried for at least 1 hour over magnesium sulfate. Once dry the magnesium sulfate was filtered from the organic which was stripped of solvent using a rotary evaporator. The final yield of viscous polymer was 100 grams. The GPC molecular weight was $Mw = 2600$ and the $Mn = 1700$ based on monodisperse polystyrene standards.

EXAMPLE 6

Ethoxylation of Poly(nonylphenol glycidyl ether)

To a 500 milliliter stainless steel Zipperclave was added 60.0 grams (0.035 moles based on an approximate molecular weight of 1700 gram/mole) of the resin prepared in Example 5 along with 0.5 grams of potassium hydroxide. The vessel was attached to an automated ethoxylation unit and was heated to 50° C. The vessel was continuously purged with nitrogen for 15 minutes and was then heated to 100° C. where it was again continuously purged with nitrogen for another 15 minutes. The vessel was then heated to 140° C. and was given a series of 6 purges by pressuring the vessel up to 80 psi, and then venting. Once the venting process was complete, the vessel was pressured to 20 psi with nitrogen.

The ethylene oxide lines were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until 60.0 grams of ethylene oxide (1.362 moles) was added based on a difference weight of the feed cylinder. After the feed was complete, the reaction was allowed to continue for 1 hour after which the vessel was cooled to 60° C., purged 4 times with nitrogen to 80 psi and was dumped to a container. The final product yield was 115 grams with a theoretical yield of 120 grams. The GPC molecular weight of the product was $Mw = 3550$ and the $MN = 2930$ based on monodisperse polystyrene standards.

EXAMPLE 7

Preparation of Poly(phenyl glycidyl ether)

To a 500 milliliter round bottom equipped with an overhead stirrer, nitrogen inlet, reflux condenser, addition funnel, and temperature controller was charged 47.06 grams of phenol (500 mmoles) and 100 grams of toluene. The solution was brought to 50° C. Once heated, 1.0 milliliter (8 mmoles) of $BF_3/Et_2O$ was added using a 2 milliliter syringe. Once the acid was added, 68.18 grams of phenyl glycidyl ether (454 mmoles) was added dropwise so as to maintain a reaction temperature of 45° C.–55° C. Once the glycidyl ether was added, the solution is refluxed for 3 hours, then cooled to about 50° C.

While hot (<60° C.) the organic was transferred to a separatory funnel and was washed once with 100 milliliters of 5% sodium bicarbonate solution. The aqueous layer was drained and the organic was washed two more times with 100 milliliter portions of deionized water. The aqueous layers were decanted and the organic was dried for at least 1 hour over magnesium sulfate. Once dry the magnesium sulfate was filtered from the organic which was stripped of solvent using a rotary evaporator. The final yield of viscous polymer was 90.3 grams (with 11% unreacted phenol). The GPC molecular weight was $Mw = 470$ and the $Mn = 310$ (on average a trimer) based on monodisperse polystyrene standards.

EXAMPLE 8

Preparation of 1,3-Bis(phenoxy)-2-propanol using the Cascading Polyol Technique

To a 1 liter round bottom flask equipped with an overhead stirrer, nitrogen inlet, reflux condenser, addition funnel, and temperature controller was charged 94.11 grams of phenol (1 mole), 12.86 grams of tetraethylammonium iodide (0.05 moles), 3.00 grams of water (0.17 moles), 42.08 grams of potassium hydroxide (0.75 moles), and 250 grams of toluene. To a 100 milliliter additional funnel was charged 23.13 grams of epichlorohydrin (0.25 moles) and 50 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliters portions of deionized water. The aqueous layers were drained off, and the toluene was removed along with unreacted phenol using a rotary evaporator. The final yield of product was 64.5 grams which was 106% of theory (residual is phenol). Final product purity was about 95% as shown by GPC.

EXAMPLE 9

Dimerization of 1,3-Bis(phenoxy)-2-propanol using the Cascading Polyol Technique To a 250 milliliter round bottom flask equipped with an overhead stirrer, nitrogen inlet, reflux condenser, additional funnel, and temperature controller was charged 20.03 grams of 1,3-bis-(phenoxy)-2-propanol prepared in Example 8 (82 mmoles), 2.06 grams of tetraethylammonium iodide (8 mmoles), 0.49 grams of water (27 mmoles), 6.51 grams of potassium hydroxide (116 mmoles), and 125 grams of toluene. To a 100 milliliter addition funnel was charged 3.61 grams of epichlorohydrin (39 mmoles) and 25 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliter portions of deionized water. The aqueous layers were drained off, and the toluene was removed using a rotary evaporator. The final yield of product was 21.6 grams which was 101% of theory. GPC showed two major components of the product. The first was the starting material at about 41% ($Mn = 220$) and the second was the coupled product at about 59% ($Mn = 520$).

EXAMPLE 10

Preparation of 1,3-Bis(hexadecyloxy)-2-propanol using the Cascading Polyol Technique To a 500 milliliter round bottom flask equipped with an overhead stirrer, nitrogen inlet, reflux condenser, additional funnel, and temperature controller was charged 60.61 grams of hexadecanol (0.25 moles), 6.18 grams of tetraethylammonium iodide (0.024 moles), 1.44 grams of water (0.082 moles), 20.20 grams of potassium hydroxide (0.36 moles), and 125 grams of toluene. To a 100 milliliter addition funnel was charged 11.10 grams of epichlorohydrin (0.12 moles) and 25 grams of toluene. The solution was brought to 65° C. at which time the epichlorohydrin solution was added over a period of 15 minutes while maintaining a reaction temperature of 65° C.±5° C. The reaction was allowed to proceed for 48 hours.

After 48 hours, the solution was cooled down to room temperature. The toluene solution was washed with two 250 milliliter portions of deionized water. The aqueous layers were drained off, and the toluene was removed using a rotary evaporator. The final yield of product was 70.9 grams which is 109% of theory (residual is hexadecanol).

EXAMPLE 11

Sulfation of 1,3-Bis(nonylphenoxy)-2propanol block-(propylene oxide)$_{10}$-block-(ethylene oxide)$_{10}$ To a 250 milliliter round bottom flask equipped with an overhead stirrer, a temperature controller, and a vacuum adapter was added 75.0 grams of the material from Example 13 (49 mmoles). The kettle was then evacuated to <20 mmHg and heated to 100° C. to remove any water. After 1 hour, the kettle was cooled to 60° C. while under vacuum. When reaching 60° C., vacuum was broken with nitrogen and 5.3 grams of sulfamic acid (54 mmoles) was added. After charging the sulfamic acid, the kettle was heated to 110° C. and evacuated to <20 mmHg. The reaction was allowed to proceed for 3 hours.

At the end of the hold period, the kettle was cooled to 85° C. and vacuum was broken with nitrogen. 1.2 grams of diethanolamine (11 mmoles) was slowly added under a blanket of nitrogen. This solution was stirred for 30 minutes. 10 grams of ethanol was added to the kettle and the temperature was regulated to 55° C. This solution was stirred for 30 minutes. The heat was removed from the kettle and 30 grams of water along with 20 grams of ethanol were added while maintaining good agitation. The solution was stirred for 15 minutes or until cooled to room temperature (<35° C.).

The pH was checked by dissolving 2 grams of the product solution in 18 grams of deionized water. If the pH was below 6.5, 0.2 gram increments of diethanolamine was added until the pH is between 6.5 and 7.5.

EXAMPLE 12

Preparation of 1,3-Bis(nonylphenoxy)-2-propanol-block-(propylene oxide)$_{10}$

To a 500 milliliter stainless steel Zipperclave was added 100.0 grams (0.202 moles) of 1,3-bis(nonylphenoxy)-2-propanol prepared in Example 1 along with 0.7 grams of potassium hydroxide. The vessel was attached to an automated unit and was heated to 50° C. The vessel was continuously purged with nitrogen for 15 minutes and was then heated to 100° C. where it was again continuously purged with nitrogen for another 15 minutes. The vessel was then heated to 140° C. and is given a series of 6 purges by pressuring the vessel up to 80 psi, and then venting. Once the venting process was completed, the vessel was pressured to 20 psi with nitrogen.

Lines connected to a cylinder which had been precharged with 117.0 grams of propylene oxide (2.02 moles) were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until all of the propylene oxide had been fed. After the feed was complete, the reaction was allowed to continue for 1 hour after which the vessel was cooled to 60° C., purged 4 times with nitrogen to 80 psi and was dumped to a container. The final product yield was 211 grams with a theoretical yield of 277 grams. The GPC molecular weight of the product was Mw=650 and the Mn=490 based on monodisperse polystyrene standards.

EXAMPLE 13

Preparation of 1,3-Bis(nonylphenoxy)-2-propanol-block-(propylene oxide)$_{10}$-block-(ethylene oxide)$_{10}$ To a 500 milliliter stainless steel Zipperclave was added 75.0 grams of the propoxylate prepared in Example 12 (0.070 moles) along with 0.3 grams of potassium hydroxide. The vessel was attached to an automated ethoxylation unit and was heated to 50° C. The vessel was continuously purged with nitrogen for 15 minutes and was then heated to 100° C. where it was again continuously purged with nitrogen for another 15 minutes. The vessel was then heated to 140° C. and was given a series of 6 purges by pressuring the vessel up to 80 psi, and then venting. Once the venting process was completed, the vessel was pressured to 20 psi with nitrogen.

The ethylene oxide lines were opened to the motor valves along with the main feed line on the Zipperclave. The feed was continued and the vessel pressure was regulated at 55 psi and a temperature of 140° C. The automation was designed to hold the temperature and the pressure within safe operating limits while addition of ethylene oxide proceeded through a pair of motor control valves. The feed was allowed to continue until 30.7 grams ethylene oxide (0.696 moles) was added based on a difference weight of the feed cylinder. After the feed was complete, the reaction is allowed to continue for 1 hour after which the vessel was cooled to 60° C., purged 4 times with nitrogen to 80 psi and was dumped to a container. The final product yield was 99 grams with a theoretical yield of 106 grams.

EXAMPLE 14

Preparation of Bis(nonylphenoxy) Adduct of 1,4-Butanediol Diglycidyl Ether

TO a five neck, two liter round bottom flask equipped with an addition funnel, thermometer, nitrogen dispersant tube, mechanical stirrer, and a decanting head with a water-cooled condenser were added 506.8 grams (2.30 mole) of nonylphenol and 350 milliliters of cyclohexane. The solution was heated to reflux, and 6.5 grams (1.3 weight percent based on nonylphenol) of potassium hydroxide in 15 milliliters of water was slowly added to the round bottom flask. After all the water was recovered in the decanting head (15 milliliters+2 milliliters formed), 220 grams (1.09 mole) of 1,4-butanediol diglycidyl ether was added dropwise between 60 and 80° C. After the addition was complete, the solution was refluxed for four hours. The contents of the flask were then washed with a five percent aqueous solution of phosphoric acid, and the organic layer was separated from the water layer and washed twice with deionized water. The reaction mixture was then placed in a one liter round bottom flask, and the remaining cyclohexane and unreacted nonylphenol were recovered by distillation, first at atmospheric pressure, then under vacuum at 0.2 mm Hg. The kettle temperature was not allowed to exceed 180° C. during the distillation to prevent discoloration of the product. The concentrated solution was then refiltered to give 710 grams of a pale-yellow liquid. Molecular weight by end-group MW analysis was 689.9 (theoretical MW=643.0). Ir and nmr spectra were consistent with the expected structure of the product.

EXAMPLE 15

Preparation of 3 Mole Ethoxylate of 1,3-Bis(nonylphenoxy)-2-propanol

To a five hundred milliliter Zipperclave reactor were charged, under nitrogen, 200.1 grams (0.43 mole) of 1,3-bis(nonylphenoxy)-2-propanol prepared in Example 2 and 0.20 grams (0.1 weight percent) of $BF_3.Et_2O$. The reaction mixture was heated to 80° C., and 55.1 grams (1.25 mole) of ethylene oxide was fed to the reactor over a two hour period. After all the ethylene oxide was fed, the reaction mixture was allowed to cook out for one hour and then dumped hot, under nitrogen, into a jar containing 160 milliliters of a one percent aqueous solution of sodium hydroxide. The organic layer was separated from the water layer and washed twice with deionized water. The washes were performed at 90° C. to facilitate the separation of the two layers. The product was then dried by azeotropic removal of the water, using cyclohexane (300 milliliters) as the entrainer. The cyclohexane was stripped off under vacuum to give a pale-yellow liquid with a molecular weight by end-group MW analysis of 601.7 (theoretical MW=629). Ir and nmr spectra were consistent with the expected structure of the product.

EXAMPLE 16

Preparation of 8 Mole Ethoxylate of Bis(nonylphenoxy) Adduct of 1,4-Butanediol Diglycidyl Ether TO a five hundred milliliter Zipperclave reactor were charged, under nitrogen, 150.2 grams (0.22 mole) of bis(nonylphenoxy) adduct of 1,4-butanediol diglycidyl ether prepared in Example 14 and 0.30 grams (0.2 weight percent) of $BF_3.Et_2O$ . The reaction mixture was heated to 80° C., and 77.5 grams (1.76 mole) of ethylene oxide was fed to the reactor over a two hour period. After all the ethylene oxide was fed, the reaction mixture was allowed to cook out for one hour and then dumped hot, under nitrogen, into a jar containing 160 milliliters of a one percent aqueous solution of sodium hydroxide. The organic layer was separated from the water layer and washed twice with deionized water. The washes were performed at 90° C. to facilitate the separation of the two layers. The product was then dried by azeotropic removal of the water, using cyclohexane (300 milliliters) as the entrainer. The cyclohexane was stripped off under vacuum to give a pale-yellow liquid with a molecular weight by end-group MW analysis of 1047 (theoretical MW=995). Ir and nmr spectra were consistent with the expected structure of the product.

Although the invention may have been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A polysaccharide having one or more complex hydrophobic groups covalently bonded thereto in which the Complex hydophobic groups are derived from a compound represented by the formula selected from:

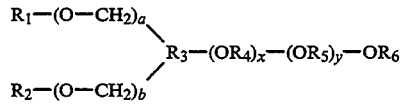

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or heaving greater than 2 pendant carbon atoms in the case of $R_3$, $R_4$ and $R_5$; or

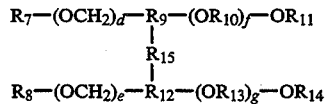

wherein $R_7$ and $R_8$ are the same or different and are hydrogen or a substituted or unsubstituted monovalent hydrocarbon residue, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are the same or different and are hydrogen, a substituted or unsubstituted monovalent hydrocarbon residue or an ionic substituent, $R_{15}$ is a substituted or unsubstituted divalent hydrocarbon residue, d and e are the same or different and are a value of 0 or 1, and f and g are the same or different and are a value of 0or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ an $R_{14}$ or having greater than 2 pendant carbon atoms in the case of $R_9$, $R_{10}$, $R_{12}$, $R_{13}$ and $R_{15}$.

2. The polysaccharide of claim 1 having repeating units represented by the structural formula:

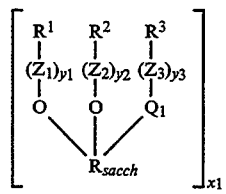

wherein for each repeating unit individually:
$Q_1$ is

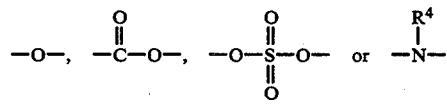

wherein R[4] is

or a mixture of hydrogen and

$R_{sacch}$ is the residue of a polysaccharide repeat unit and may include additional reactive groups;

$x_1$ is from about 50 to about 20,000;

each $Y_1$, $Y_2$ and $Y_3$ is 0 or 1;

each $Z_1$, $Z_2$ and $Z_3$ is a divalent connecting segment; and each $R^1$, $R^2$ and $R^3$ is individually a hydrogen, a substituted or unsubstituted hydrocarbon residue or a nitrogen-, oxygen-, sulfur- or carboxyl-containing hydrocarbon residue or $R_h$, wherein $R_h$ is the residue of a substituted or unsubstituted complex hydrophobe compound; provided that when $R^1$, $R^2$ or $R^3$ is hydrogen then $Y_1$, $Y_2$ or $Y_3$ respectively is 0, and one or more repeating units have one or more $R^1$, $R^2$ or $R^3$ which is $R_h$.

3. The polysaccharide of claim 1 having bunching of hydrophobic groups, complex hydrophobic groups or mixtures thereof.

4. The polysaccharide of claim 3 wherein each hydrophobe bunch contains at least two hydrophobic groups, complex hydrophobic groups or mixtures thereof which are separated from each other by no more than about 50 covalently bonded sequentially connected atoms.

5. The polysaccharide of claim 1 wherein $R_1$, $R_2$, $R_7$ and $R_8$ are selected from substituted or unsubstituted alkyl, aryl, alkylaryl, arylalkyl, cycloalkyl or mixtures thereof.

6. The polysaccharide of claim 5 wherein $R_1$, $R_2$, $R_7$ and $R_8$ are selected from dodecylphenyl, nonylphenyl, octylphenyl or mixtures thereof.

7. The polysaccharide of claim 1 wherein at least one of $R_1$, $R_2$, $R_7$ and $R_8$ is a hydrocarbon radical represented by the formula:

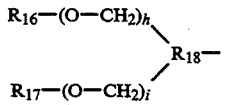

wherein $R_{16}$ and $R_{17}$ are the same or different and are hydrogen or a substituted or unsubstituted monovalent hydrocarbon residue, $R_{18}$ is a substituted or unsubstituted divalent or trivalent hydrocarbon residue, and h and i are the same or different and are a value of 0 or 1.

8. The polysaccharide of claim 1 wherein at least one of $R_4$, $R_5$, $R_{10}$ and $R_{13}$ is a hydrocarbon radical represented by the formula:

wherein each $R_{19}$ is the same or different and is a substituted or unsubstituted divalent hydrocarbon residue, $R_{20}$ is hydrogen, a substituted or unsubstituted monovalent hydrocarbon residue or an ionic substituent, and j is a value of 0 or greater.

9. The polysaccharide of claim 1 wherein each $R_4$, $R_5$, $R_{10}$ and $R_{13}$ is selected from $-CH_2CH_2-$, $-CH_2CH(CH_3)-$ or mixtures thereof.

10. The polysaccharide of claim 1 wherein $R_6$, $R_{11}$ and $R_{14}$ are hydrogen.

11. The polysaccharide of claim 1 wherein the values of x, y, f and g are from 0 to about 200 or greater.

12. The polysaccharide of claim 1 wherein $R_{15}$ is selected from -phenylene-$(CH_2)_m(Q)_n(CH_2)_m$-phenylene- and -naphthylene-$(CH_2)_m(Q)_n(CH_2)_m$-naphthylene-, wherein Q individually represents a substituted or unsubstituted divalent bridging group selected from $-CR_{21}R_{22}-$, $-O-$, $-S-$, $-NR_{23}-$, $-SiR_{24}R_{25}-$ and $-CO-$, wherein $R_{21}$ and $R_{22}$ individually represent a radical selected from hydrogen, alkyl of 1 to 12 carbon atoms, phenyl, tolyl and anisyl; $R_{23}$, $R_{24}$ and $R_{25}$ individually represent a radical selected from hydrogen and methyl, and each m and n individually have a value of 0 or 1.

13. The polysaccharide claim 2 wherein the complex hydrophobic group is attached via an ether linkage.

14. The polysaccharide of claim 2 which is cellulose, wherein $Q_1$ is oxygen.

15. The polysaccharide of claim 14 wherein at least one of $R^1$, $R^2$ or $R^3$ is hydroxyethyl.

16. A process for producing a polysaccharide having one or more complex hydrophobic groups covalently bonded thereto which comprises reacting an ether-substituted polysaccharide with a complex hydrophobe-containing compound wherein the ether substitution on the polysaccharide provides an increase in the amount of complex hydrophobe substituent reacted onto the polysaccharide as compared to the corresponding polysaccharide absent such ether substitution in which the complex hydophobic groups are derived from a compound represented by the formula selected from:

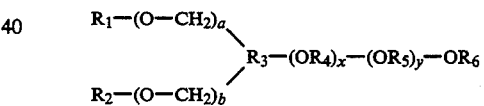

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$; or

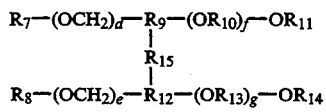

wherein $R_7$ and $R_8$ are the same or different and are hydrogen or a substituted or unsubstituted monovalent hydrocarbon residue, $R_9$ and $R_{12}$ are the same or different and a are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are the same or different and are hydrogen, a substituted or unsubstituted monovalent hydrocarbon residue or an ionic substituted, $R_{15}$ is a substituted or unsubstituted divalent hydrocarbon residue, d and e are the same or different and are a value of 0 or 1, and f and g are the same or different and are a of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ an $R_{14}$ or having greater than 2 pendant carbon atoms in the case of $R_9$, $R_{10}$, $R_{12}$, $R_{13}$ and $R_{15}$.

17. The process of claim 16 wherein the polysaccharide ether is hydroxyethyl cellulose and the complex hydrophobe-containing compound is an alkylaryl glycidyl ether.

18. A polysaccharide produced by the process of claim 16.

19. A process for producing a polysaccharide having one or more complex hydrophobic groups covalently bonded thereto which comprises reacting a polysaccharide with a complex hydrophobe-containing glycidyl ether compound in which the complex hydophobic groups are derived from a compound represented by the formula selected from:

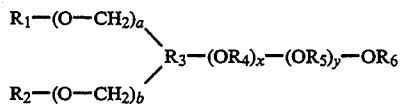

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$; or

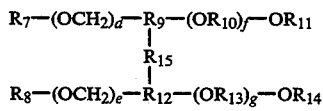

wherein $R_7$ and $R_8$ are the same or different and are hydrogen or a substituted or unsubstituted monovalent hydrocarbon residue, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are this same or different and are hydrogen, a substituted or unsubstituted monovalent hydrocarbon residue or an ionic substituent, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ and $R_{14}$ or having greater than 2 pendant carbon atoms in the case of $R_9$, $R_{10}$, $R_{12}$, $R_{13}$ and $R_{15}$.

20. The process of claim 19 wherein the polysaccharide is hydroxyethyl cellulose, and the complex hydrophobe-containing compound is bis-nonyl phenyl glycidyl ether.

21. A polysaccharide produced by the process of claim 19.

22. A latex composition containing water, latex polymer and water-soluble polysaccharide with one or more complex hydrophobic groups covalently bonded thereto in which the complex hydophobic groups are derived from a compound represented by the formula selected from:

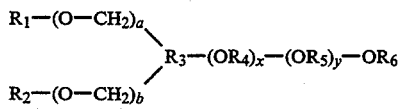

wherein $R_1$ and $R_2$ are the same or different and are hydrogen or a substituted or unsubstituted monovalent hydrocarbon residue, $R_3$ is a substituted or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case of $R_3$, $R_4$ and $R_5$; or

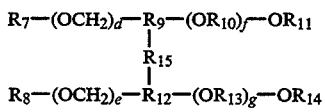

wherein $R_7$ and $R_8$ are the same or different and are hydrogen or a substituted or unsubstituted monovalent hydrocarbon residue, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are the same or different and are hydrogen, a substituted or unsubstituted monovalent hydrocarbon residue or an ionic substituent, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the case of $R_7$, $R_8$, $R_{11}$ an $R_{14}$ or having greater than 2 pendant carbon atoms in the case of $R_9$, $R_{10}$, $R_{12}$, $R_{13}$ and $R_{15}$.

23. A process for producing a latex composition containing water and latex polymer with improved theology and/or stability which comprises providing the latex with a water-soluble polysaccharide having one or more complex hydrophobic groups covalently bonded thereto in which the complex hydophobic groups are derived from a compound represented by the formula selected from:

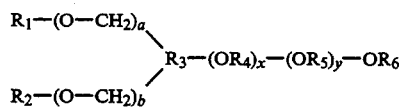

wherein $R_1$ and $R_2$ are the same or different and are hydrogen or a substituted or unsubstituted monovalent hydrocarbon residue, $R_3$ is a substitute or unsubstituted divalent or trivalent hydrocarbon residue, each $R_4$ is the same or different and is a substituted or unsubstituted divalent hydrocarbon residue, each $R_5$ is the same or different and is a substituted or unsubstituted divalent hydrocarbon residue, $R_6$ is hydrogen, a substituted or unsubstituted monovalent hydrocarbon residue or an ionic substituent, a and b are the same or different and are a value of 0 or 1, and x and y are the same or different and are a value of 0 or greater; provided at least two of $R_1$, $R_2$, $R_3$, $R_4$, $R_5$ and $R_6$ are a hydrocarbon residue having greater than 2 carbon atoms in the case of $R_1$, $R_2$ and $R_6$ or having greater than 2 pendant carbon atoms in the case $R_3$, $R_4$ and $R_5$; or

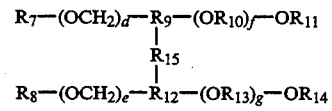

wherein $R_7$ and $R_8$ are the same or different and are hydrogen or a substituted or unsubstituted monovalent hydrocarbon residue, $R_9$ and $R_{12}$ are the same or different and are a substituted or unsubstituted divalent or trivalent hydrocarbon residue, each $R_{10}$ is the same or different and is a substituted or unsubstituted divalent hydrocarbon residue, each $R_{13}$ is the same or different and is a substituted or unsubstituted divalent hydrocarbon residue, $R_{11}$ and $R_{14}$ are the same or different and are hydrogen a substituted or unsubstituted monovalent hydrocarbon residue or an ionic substituent, $R_{15}$ is a substituted or unsubstituted divalent hydrocarbon residue, d and e are the same or different and are a value of 0 or 1, and f and g are the same or different and are a value of 0 or greater; provided at least two of $R_7$, $R_8$, $R_9$, $R_{10}$, $R_{11}$, $R_{12}$, $R_{13}$, $R_{14}$ and $R_{15}$ are a hydrocarbon residue having greater than 2 carbon atoms in the same case of $R_7$, $R_8$, $R_{11}$ an $R_{14}$ or having greater than 2 pendant carbon atoms in the case of $R_9$, $R_{10}$, $R_{12}$, $R_{13}$ and $R_{15}$.

24. A process of thickening an aqueous system comprising adding to the system a water-soluble polysaccharide of claim 1.

25. The process of claim 24 wherein the system is thickened further by the addition of an effective amount of surfactant, solvent or non-solvent.

* * * * *